United States Patent [19]

Miyamoto et al.

[11] 4,039,852
[45] Aug. 2, 1977

[54] EXHALATION INSPECTING APPARATUS

[75] Inventors: Keiichi Miyamoto; Naohiko Inoue, both of Yokohama, Japan

[73] Assignee: Nissan Motor Co., Ltd., Yokohama, Japan

[21] Appl. No.: 584,049

[22] Filed: June 5, 1975

[30] Foreign Application Priority Data

June 18, 1974 Japan .............................. 49-70287[U]

[51] Int. Cl.$^2$ ....................... H01H 35/00; H02H 3/00
[52] U.S. Cl. ................................. 307/326; 307/10 R; 340/279; 128/2 C
[58] Field of Search .................. 307/94, 10 R, 10 AT; 340/279, 53, 54, 64; 180/99; 128/2 C

[56] References Cited

U.S. PATENT DOCUMENTS

3,780,311  12/1973  Brown ............................... 307/10 R

*Primary Examiner*—Herman J. Hohauser

[57] ABSTRACT

Herein disclosed is an exhalation inspecting apparatus for use, for example, with a device mounted on an automotive vehicle for producing warning signals or disabling the vehicle from being started from rest condition if the inspecting apparatus detects an alcohol concentration higher than an allowable limit in air exhaled by a subject or an intending driver. The inspecting apparatus is responsive not only to the alcohol concentration of the subject's exhaled air but to breakage of electric lines connected to detecting elements incorporated in the inspecting apparatus and causes the warning or locking device to be operative in case the electric lines happen to be broken.

19 Claims, 3 Drawing Figures

EXHALATION INSPECTING APPARATUS

The present invention relates generally to an exhalation inspecting apparatus for detecting an alcohol concentration, if any, of subject's exhaled air and, more particularly, to an exhalation inspecting apparatus which may be combined with a warning or locking device of a vehicle to produce warning signals or to hold the vehicle inoperative when actuated by the inspecting apparatus responding to an alcohol concentration exceeding a predetermined allowable limit.

Alcohol impairs a vehicle driver's judgement and performance and as a result the drunken driver is a significant cause of serious injury and death as is well known. Exhalation inspecting means have therefore been developed so as to enable an intending driver to make an on-the-spot inspection of the alcohol concentration of the exhaled air. In some modern automotive vehicles, the exhalation inspecting means is combined with a warning or locking device which produces warning signals or disables the vehicle from being started against the intending driver's will if the alcohol concentration detected by the inspecting means is higher than a predetermined allowable limit to assure the driver's performance.

The exhalation inspecting means of this nature comprises an exhalation blow-in tube into which a subject or, in this instance, the intending driver of the vehicle is to blow exhaled air and an electric circuit arrangement to actuate the warning or locking device when the subject's exhaled air is found to contain an alcohol concentration over a predetermined allowable limit. The circuit arrangement includes detecting elements positioned within the exhalation blow-in tube so as to detect the alcohol concentration, if any, of the exhaled air blown into the blow-in tube and to produce electrical signals indicative of the detected alcohol concentration. The detecting elements are connected to other essential elements of the circuit arrangement through wires forming a single flexible cord leading from the blow-in tube. Because of the fact that the blow-in tube and accordingly the flexible cord leading therefrom are frequently moved into and out of thier housed conditions, the wires contained in the flexible cord are subject to breakage during use of the inspecting means. In some cases, the cord may be purposely broken by those who are unwilling to effect the cumbersome operation required for the alcohol inspection. When the wires connected to the detecting element of the inspecting means are thus broken, the inspecting means will fail to function properly and would produce misleading or erroneous signals. The present invention contemplates elimination of such a drawback which has been inherent in the prior art exhalation inspecting means.

It is, therefore, a primary object of the present invention to provide an improved exhalation inspecting apparatus which is responsive not only to the alcohol concentration of exhaled air but also to breakage of the wires connected to the detecting elements of the inspecting apparatus.

In accordance with the present invention, such an object will be accomplished in an exhalation inspecting apparatus which comprises power supply means, an alcohol level detecting circuit connected to the power supply means by a first set of wires and operative to produce a first output voltage indicative of an alcohol concentration of air exhaled by a subject and a second output voltage indicative of the volume of the subject's exhaled air, a discriminating circuit connected to the alcohol level detecting circuit by a second set of wires and operative to produce a first output signal if the first output voltage is indicative of an alcohol concentration lower than a predetermined allowable limit and the second output voltage is indicative of a volume of exhaled air larger than a predetermined minimum limit and a second output signal if the first output voltage is indicative of an alcohol concentration higher than the predetermined allowable limit and/or the second output voltage is indicative of a volume of exhaled air smaller than the predetermined minimum limit, a wire breakage detecting circuit responsive to breakage of any one of the wires and operative to produce a first output signal in the absence of breakage in the wires and a second output signal in response to breakage of at least one of the wires, and a control circuit responsive to the signals from the discriminating circuit and the wire breakage detecting circuit for producing a first output signal in the presence of both of the first output signals from the discriminating circuit and the wire breakage detecting circuit and a second output signal in the presence of at least one of the second output signals from the discriminating circuit and the wire breakage detecting circuit.

In accordance with one specific aspect of the present invention, the power supply means has first and second output terminals and the alcohol level detecting circuit has first and second input terminals connected to the first and second output terminals of the power supply means through the first set of wires respectively and first and second output terminals connected to the discriminating circuit through the second set of wires, wherein the alcohol level detecting circuit comprising first detecting means connected between the first input and output terminals of the alcohol level detecting circuit and responsive to breath containing alcohol in the subject's exhaled air for delivering the first output voltage from the first output terminal of the alcohol level detecting circuit and second detecting means connected between the second input and output terminals of the alcohol level detecting circuit and responsive to the volume of the subject's exhaled air for delivering the second output voltage from the second output terminal of the alcohol level detecting circuit.

In accordance with another specific aspect of the present invention, the alcohol level detecting circuit comprises first detecting means operative to produce the output voltage which has a tendency to increase as the detected alcohol concentration increases and second detecting means operative to produce the second output voltage which has a tendency to diminish as the detected volume of the exhaled air increases, wherein the discriminating circuit comprising first comparing means for being supplied with the first output voltage and with a first reference voltage indicative of the predetermined allowable limit of the alcohol concentration and producing a first output signal if the first output voltage is lower than the first reference voltage and a second output signal if the first output voltage is higher than the first reference voltage, second comparing means for being supplied with the second output voltage and with a second reference voltage indicative of the predetermined minimum limit of the volume of the exhaled air and producing a first output signal if the second output voltage is lower than the second reference voltage and a second output signal if the second output voltage is higher than the second reference voltage, and circuit means for producing the first output signal of the discriminating circuit in the presence of both of the first output signal from the first and second comparing means and the second output signal of the discriminating circuit in the presence of at least one of the second output signals from the first and second comparing means.

In accordance with still another specific aspect of the present invention, the power supply means has first and second output terminals and the alcohol level detecting circuit has first and second input terminals connected to the first and second output terminals through the first set of wires, respectively, and first and second output terminals connected to the discriminating circuit through the second set of wires, wherein the wire breakage detecting circuit comprising first switching means connected to the first output terminal of the power supply means and having a control electrode connected to the first input terminal through the first output terminal of the alcohol level detecting circuit for rendering the first switching means conductive in the absence of breakage in each of the wires connected to the first input and output terminals of the alcohol level detecting circuit and non-conductive in the presence of breakage in at least one of the wires connected to the first input and output terminals of the alcohol level detecting circuit, second switching means connected to the second output terminal of the power supply means and having a control electrode connected to the second input terminal through the second output terminal of the alcohol level detecting circuit for rendering the second switching means conductive in the absence of breakage in each of the wires connected to the second input and output terminals of the alcohol level detecting circuit and non-conductive in the presence of breakage in at least one of the wires connected to the second input and output terminals of the alcohol level detecting circuit, and circuit means having first and second input terminals respectively connected over the first and second switching means to the first and second output terminals of the power supply means for producing the first output signal of the wire breakage detecting circuit when both of the first and second switching circuits are conductive and the second output signal of the wire breakage detecting circuit when at least one of said first and second switching means is non-conductive.

The features and advantages of the exhalation inspecting apparatus according to the present invention will become more apparent from the following description taken in conjunction with the accompanying drawings, in which.

Figure 1:
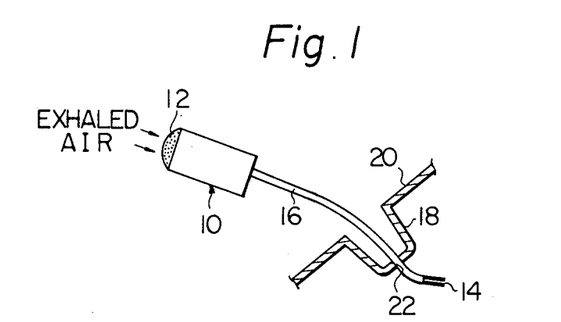
FIG. 1 is a side elevation view showing, partially in section, a blow-in arrangement forming part of a preferred embodiment of the exhalation inspecting apparatus according to the present invention.

Reference will now be made to the drawings, first to FIG. 1 which shows a blow-in tube 10 forming part of the embodiment of the exhalation inspecting apparatus according to the present invention. The blow-in tube 10 has a pored or otherwise open end portion 12 through which a subject or, in this context, an intending driver of the vehicle equipped with the inspecting apparatus is to blow into the tube 10 for the detection of the alcohol content, if any, of the exhaled air. The blow-in tube 10 has incorporated therein electric detecting elements (not shown in FIG. 1) which produce electrical signals responsive to exhaled air blown into the tube 10, as will be discussed in more detail. The detecting elements are connected to lines or wires 14 which lead from the end of the blow-in tube 10 opposite to the pored end portion 12 and which are electrically insulated from each other. The lines or wires 14 are wrapped in a protective and insulating sheath to form a single flexible cord 16. The blow-in tube 10 may be housed, when unused, within a generally cup-shaped receptacle 18 which is formed in an upper wall portion 20 of a console box secured to a structural part of the vehicle and which is located to provide a subject or an intending driver of the vehicle with easy access to the blow-in tube 10. The receptacle 18 has formed in its bottom wall a hole 22 through which the flexible cord 16 tailed to the blow-in tube 10 longitudinally movably extends into the console box. The cord 16 is preferably rolled on a rotatable reel (not shown) which is biased to urge the cord 16 to retract inwardly of the upper wall portion 20 of the console box so that the cord 16 is at all times maintained taut between the blow-in tube 10 and the reel and is thus prevented from being entangled irrespective of the position of the blow-in tube 10 relative to the receptacle. The lines or wires 14 forming the flexible cord 16 are, thus, suscepticle to breakage when the blow-in tube 10 is moved into and out of the receptacle 18 so that the cord 16 is pulled outwardly or retracted inwardly.

Figure 2:
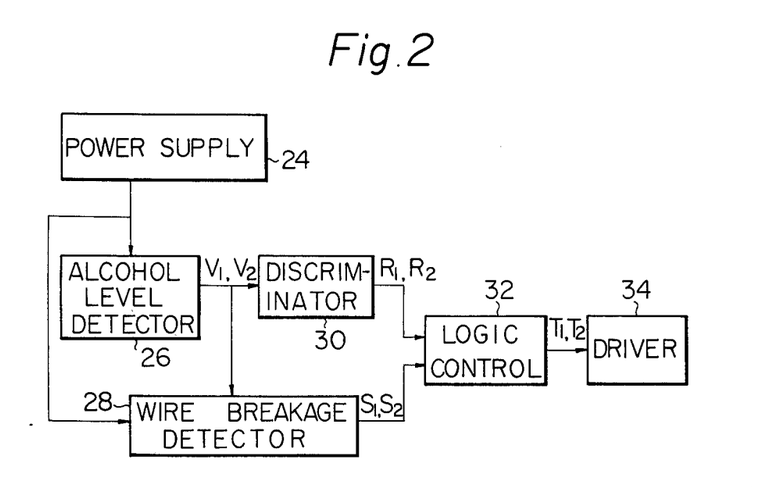
FIG. 2 is a block diagram showing an electrical circuit arrangement of the exhalation inspecting apparaus embodying the present invention.

FIG. 2 diagrammatically illustrates an electric circuit to which the lines or wires 14 leading from the blow-in tube 10 are connected. The electric circuit comprises a d.c. power source circuit 24 to produce output voltages of predetermined magnitudes when a subject or an intending driver of the vehicle is seated on the driver's seat and is prepared to operate the vehicle. The output voltages thus delivered from the d.c. power source 24 are supplied to an alcohol level detecting circuit 26 and a wire breakage detecting circuit 28. The alcohol level detecting circuit 26 comprises the previously mentioned detecting elements positioned within the blow-in tube 10 shown in FIG. 1 and delivers a first output voltage $V_1$ which is indicative of the concentration of alcohol contained, if any, in the exhaled air blown into the blow-in tube 10 and a second output voltage $V_2$ signal which is produced responsive to the volume of the exhaled air blown into the tube 10 irrespective of the presence or absence of alcohol in the exhaled air. The output voltages $V_1$ and $V_2$ thus produced by the alcohol level detecting circuit 26 are supplied to a discriminating circuit 30 which is arranged to produce a first output signal $R_1$ if the first output voltage $V_1$ from the alcohol level detecting circuit 26 is representative of an alcohol concentration lower than a predetermined level or of the absence of alcohol in the exhaled air inspected and if the second output voltage $V_2$ of the detecting circuit 26 is indicative of a volume larger than a predetermined limit of the exhaled air blown into the blow-in tube 10 (FIG. 1) and a second output signal $R_2$ if the first output voltage $V_1$ from the alcohol level detecting circuit 26 is representative of an alcohol concentration which is higher than the above-mentioned predetermined level. If no exhaled air is blown into the blow-in tube 10 shown in FIG. 1 or if exhaled air is blown into the tube 10 only to a volume which is smaller than the above-mentioned predetermined level and is insufficient to make the result of the inspection significant and reliable, then the discriminating circuit 30 produces the second output signal $R_2$.

The alcohol level detecting circuit 26 is positioned within the previously mentioned blow-in tube 10 shown in FIG. 1 and, thus, lines connected to the input and output terminals of the detecting circuit 26, such as for example the lines connecting the detecing circuit 26 to the power source circuit 24 and the discriminating circuit 30 are among the lines which are designated by reference numeral 14 in FIG. 1 and which are therefore susceptible to breakage. The lines leading from the alcohol level detecting circuit 26 are thus connected not only to the discriminating circuit 30 but also to the wire breakage detecting circuit 28 so as to enable the latter to respond to a breakage of any of the lines 14 (FIG. 1) leading to and from the alcohol level detecting circuit 26. The wire breakage detecting circuit 28 is thus operative to produce a first output signal $S_1$ in the absence of a breakage of any of the lines or wires 14 and a second output signal $S_2$ responsive to breakage of at least one of the lines or wires 14 connected to the alcohol level detecting circuit 28.

The wire breakage detecting circuit 28 and the discriminating circuit 30 have respective output terminals connected to a logic control circuit 32 to produce a first output signal $T_1$ if both of the wire breakage detecting circuit 28 and the discriminating circuit 30 are producing their respective first output signals $S_1$ and $R_1$ concurrently and a second output signal $T_2$ if at least one of the wire breakage detecting circuit 28 and the discriminating circuit 30 is producing its second output signal $S_2$ or $R_2$. The logic control circuit 32 has an output terminal connected to a driver circuit 34 which in turn has an output terminal connected to electrically operated actuating means of a locking device (not shown) which disables the vehicle from being started with the engine not running. The locking device to achieve such an end is, per se, well known in the art and may be designed in any of numerous manners so as to maintain the ignition system of the vehicle de-energized or to hold the steering or power transmission system of the vehicle locked or otherwise inoperative when the locking device is actuated by the driver circuit 34. The driver circuit 34 is arranged to hold the locking device inoperative in response to the first output signal $T_1$ from the logic control circuit 32 and to actuate the locking device in response to the second output signal $T_2$ from the logic control circuit 32.

Figure 3:
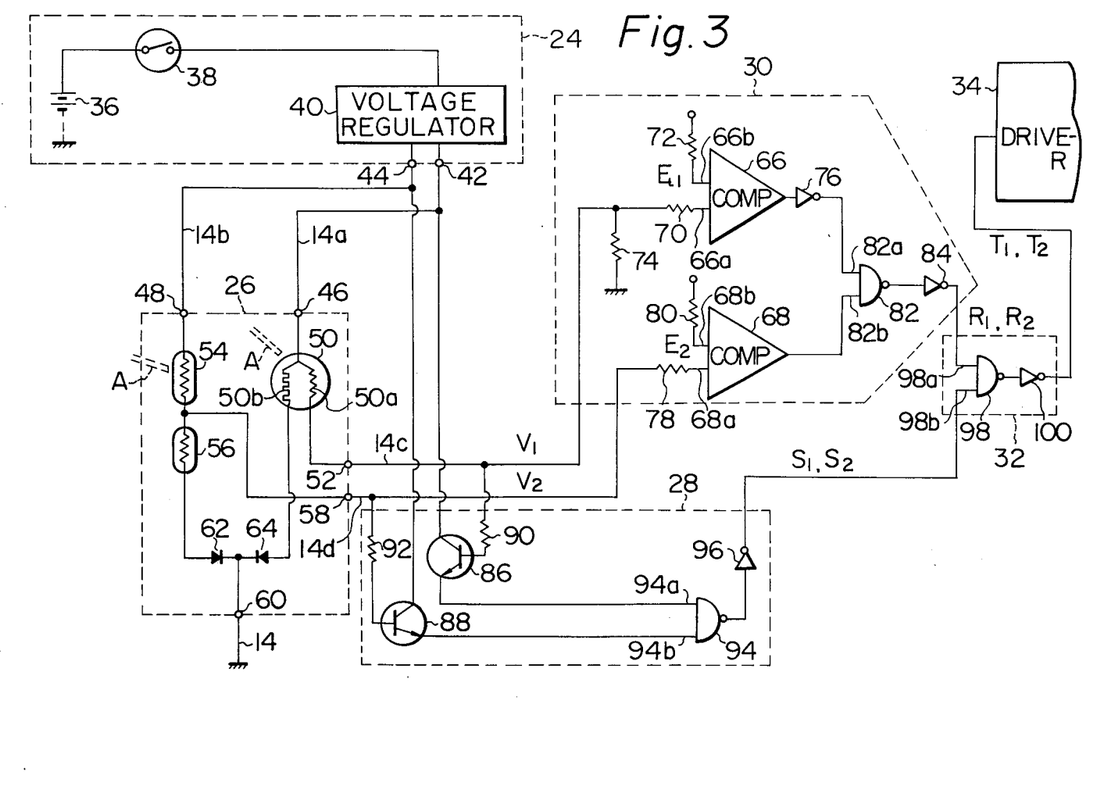
FIG. 3 is a schematic view showing details of the circuit arrangement illustrated in FIG. 2.

FIG. 3 illustrates details of the circuits 24, 26, 28, 30 and 32 providing the functions thus far described.

Referring to FIG. 3, the d.c. power source circuit 24 comprises a d.c. power source 36 which may be the storage battery incorporated into the vehicle for powering various electrically operated devices and instruments provided in the vehicle. The d.c. power source or storage battery 36 has a negative terminal grounded and a positive terminal connected across a normally open switch 38 to a voltage regulator 40. The normally open switch 38 is preferably linked with a switch responsive to a locked condition of a door of the vehicle and a switch responsive to a seated condition of a subject or, in this instance, an intending driver of the vehicle, though not shown in the drawings. The normally open switch 38 thus arranged is closed when the door of the vehicle is fully closed and locked from an open condition and furthermore the subject or intending driver is seated on the driver's seat of the vehicle. The voltage regulator 40 steps up or down the voltage supplied from the d.c. power source 36 through the switch 38 thus closed. The voltage regulator has first and second output terminals 42 and 44 through each of which the voltage thus modified by the voltage regulator 40 is delivered when the switch 38 is closed. The voltage regulator 40 may be readily designed as desired by those skilled in the art and, for this reason, no detailed circuit arrangement thereof is herein illustrated.

On the other hand, the alcohol level detecting circuit 26 positioned within the blow-in tube 10 illustrated in FIG. 1 has first and second input terminals 46 and 48 which are connected to the first and second output terminals 42 and 44 of the above described voltage regulator 40 by way of lines or wires 14a and 14b, respectively. The lines or wires 14a and 14b are two of the lines or wires 14 forming the flexible cord 16 leading from the blow-in tube 10 shown in FIG. 1 and are thus susceptible to breakage when the blow-in tube 10 is moved into and out of the receptacle 18 and the flexible cord 16 is stretched. The alcohol level detecting circuit 26 comprises an alcohol sensing unit 50 which consist of a conventional alcohol-sensitive element 50a the resistance of which is reduced when heated and subjected to an alcoholic atmosphere and a heating element 50b which produces heat when energized and which is located in the vicinity of the alcohol-sensitive element 50a for heating the alcohol-sensitive element 50a by the heat thus produced. The alcohol-sensitive elements 50a and 50b of the alcohol sensing unit 50 are connected each at one end in parallel with the first input terminal 46 of the detecting circuit 26. The alcohol-sensitive element 50a is connected at the other end to a first output terminal 52 of the detecting circuit 26. The alcohol level detecting circuit 26 further comprises first and second temperature-sensitive resistance-variable semi-conductor elements such as thermistors 54 and 56 which are connected in series to the second input terminal 48 of the detecting circuit 26. The first thermistor 54 is thus connected at one end to the second input terminal 48 of the detecting circuit 26 and at the other end to not only to one end of the second thermistor 56 but also to a second output terminal 58 of the detecting circuit 26 as shown. The second thermistor 56 and the heating element 50b of the alcohol sensing unit 50 are connected to each other at the other ends in parallel and with a third output terminal 60 of the detecting circuit 26 through diodes 62 and 64, respectively, which are connected mutually in forward directions to each other. Lines or wires 14c, 14d and 14e lead from the first, second and third output terminals 52, 58 and 60, respectively, of the alcohol level detecting circuit 26 thus constructed and arranged. The lines or wires 14c, 14d and 14e are also among the lines or wires 14 forming the flexible cord 16 shown in FIG. 1 and are thus susceptible to breakage when the blow-in tube 10 is moved into and out of the receptacle 18.

The resistance of the alcohol-sensitive element 50a of the sensing unit 50 is reduced in proportion to the concentration of alcohol contained in exhaled air blown onto the sensing unit 50 as indicated by arrow A so that the previously mentioned output voltage $V_1$ indicative of the detected alcohol concentration appears at the first output terminal 52 of the detecting circuit 26. On the other hand, the resistance of the first thermistor 54 is increased when cooled. When, thus, the first thermistor 54 receives exhaled air as indicated also by the arrow A is consequently cooled down from its initial temperature, the resistance of the thermistor 54 increases in proportion to the volume of the exhaled air contacting the thermistor 54 so that the previously mentioned output voltage $V_2$ indicative of the volume of the exhaled air blown into the blow-in tube 10 shown in FIG. 1 appears at the second output terminal 58 of the detecting circuit 26. The above-mentioned first and second diodes 62 and 64 have respective anode terminals connected to the second thermistor 56 and the heating element 50b of the alcohol sensing unit 50 and have respective cathode terminals connected in parllel to the third output terminal 60 of the detecting circuit 26. The third output terminal 60 is grounded through the previously mentioned line or wire 14e.

The discriminating circuit 30 supplied with the above-mentioned output voltages $V_1$ and $V_2$ from the alcohol level detecting circuit 26 comprises first and second comparator circuits 66 and 68. The first comparator circuit 66 has first and second input terminals 66a and 66b. The first input terminal 66a of the comparator circuit 66 is connected through a resistor 70 to the line or wire 14c leading from the first output terminal 52 of the alcohol level detecting circuit 26, and the second input terminal 66b of the comparator circuit 66 is connected through a resistor 72 to a suitable source (not shown) of a positive d.c. voltage so that a predetermined reference voltage $E_1$ is applied to the comparator circuit 66 through the second input terminal 66b thereof. Between the resistor 70 and the first output terminal 52 of the alcohol level detecting circuit 26 may be connected a variable resistor 74 for the purpose of adjusting the voltage applied to the comparator circuit 66 through the first input terminal 66a thereof. The first comparator circuit 66 is operative to compare the voltage $V_1$ from the sensing unit 50 of the alcohol level detecting circuit 26 with the predetermined reference voltage $E_1$ and to produce a logic 0 signal when the input voltage $V_1$ is lower than the reference voltage $E_1$ and a logic 1 signal when the voltage $V_1$ is higher than the reference voltage $E_1$. The first comparator circuit 66 has an output terminal connected to a logic negation circuit 76 which produces a logic 1 or 0 signal responsive to the logic 0 or 1 signal, respectively, delivered from the first comparator circuit 66. On the other hand, the second comparator circuit 68 has first and second input terminals 68a and 68b. The first input terminal 68a of the comparator circuit 68 is connected through a resistor 78 to the line or wire 14d leading from the second output terminal 58 of the alcohol level detecting circuit 26, and the second input terminal 68b is connected through a resistor 80 to a suitable source (not shown) of a positive d.c. voltage so that a predetermined reference voltage $E_2$ is applied to the comparator circuit 68 through the second input terminal 68b thereof. The second comparator circuit 68 is operative to compare the voltage $V_2$ from the first thermistor 54 of the alcohol level detecting circuit 26 with the predetermined reference voltage $E_2$ and to produce a logic 0 output signal when the input voltage $V_2$ is higher than the reference voltage $E_2$ and a logic 1 output signal when the input voltage $V_2$ is lower than the reference voltage $E_2$. The reference voltage $E_1$ impressed on the first comparator circuit 66 is selected to correspond to a predetermined allowable limit of an alcohol concentration of air exhaled by an intending driver of a vehicle and the reference voltage $E_2$ impressed on the second comparator circuit 68 is selected to correspond to a predetermined minimum limit of the volume of exhaled air to be inspected as required to make the inspection reliable.

The discriminating circuit 30 further comprise a logic "NAND" gate circuit 82 which has a first input terminal 82a connected to the output terminal of the negation circuit 76 and a second input terminal 82b connected to the output terminal of the second comparator circuit 68. The logic"NAND" gate circuit 82 thus produces a logic 0 output signal when the first comparator circuit 66 is producing its logic 0 output signal and simultaneously the second comparator circuit 68 is producing its logic 1 output signal. The "NAND" gate circuit 82 produces a logic 1 output signal when the first comparator circuit 66 is producing its logic 1 output signal and/or the second comparator circuit 68 is producing its logic 0 output signal. The logic 0 or 1 output signal produced at the output terminal of the "NAND" gate circuit 82 is inverted into a logic 1 or 0 signal, respectively, by means of a logic negation circuit 84 which has an input terminal connected to the output terminal of the "NAND" gate circuit 84. The logic 1 and 0 output signals thus delivered from the negation circuit 84 correspond to the previously mentioned first and second output signals $R_1$ and $R_2$, respectively, of the discriminating circuit 30. The logic 1 output signal $R_1$ is delivered from the discriminating circuit 30 when the voltage $V_1$ supplied from the first output terminal 52 of the alcohol level detecting circuit 26 is lower than the reference voltage $E_1$ impressed on the first comparator circuit 66 and simultaneously the voltage $V_2$ supplied from the second output terminal 68 of the alcohol level detecting circuit 26 is lower than the reference voltage $E_2$ impressed on the second comparator circuit 68. The logic 0 output signal $R_2$ is delivered from the discriminating circuit 30 when the voltage $V_1$ is higher than the reference voltage $E_1$ and/or the voltage $V_2$ is higher than the reference voltage $E_2$. In other words, the discriminating circuit 30 produces its logic 1 output signal $R_1$ if the subject's exhaled air is blown into the blow-in tube 10 shown in FIG. 1 to a volume larger than the previously mentioned minimum limit and in addition the exhaled air does not contain alcohol or contains alcohol in a concentration lower than the previously mentioned allowable limit. The discriminating circuit 30 produces its logic 0 output signal "R" if a subject or intending driver fails to blow into into the blow-in tube 10 or even though the subject blows into the blow-in tube 10, the volume of the exhaled air blown into the blow-in tube is short of the predetermined minimum limit or if the exhaled air thus inspected contains alcohol in a concentration higher than the pedetermined allowable limit.

On the other hand, the wire breakage detecting circuit 28 comprises first and second transistors 86 and 88 which are shown by way of example to be of the n-p-n type. The first transistor 86 has a collector electrocde connected to the previously mentioned first output terminal 42 of the voltage regulator 40 and a base electrode connected through a resistor 90 to the previously mentioned first output terminal 52 of the alcohol level detecting circuit 26. Likewise, the second transistor 88 has a collector electrode connected to the previously mentioned second output terminal 44 of the voltage regulator 40 and a base electrode connected through a resistor 92 to the previously mentioned second output terminal 58 of the alcohol level detecting circuit 26. The wire breakage detecting circuit 28 further comprises a logic "NAND" gate circuit 94 which has a first input terminal 94a connected to the emitter electrode of the first transistor 86 and a second input terminal 94b connected to the emitter electrode of the second transistor 88. The logic "NAND" gate circuit 94 is thus operative to produce a logic 0 signal when both of the first and second transistors 86 and 88 are conductive and to produce a logic 1 output signal when at least one of the transistors 86 and 88 is non-conductive. The transistors 86 and 88 have their respective base electrodes connected to the alcohol level detecting circuit 26 through the lines or wires 14c and 14d which are in series with the lines or wires 14a and 14b, respectively, so that the first transistor 86 will be rendered non-conductive if at least one of the lines or wires 14a and 14c is broken and likewise the second transistors 88 will be rendered non-conductive if at least one of the lines or wires 14b and 14d is broken. The "NAND" gate circuit 94 thus produces its logic 1 output signal in the event at least one of the lines or wires 14a, 14b, 14d and 14e connected to the alcohol level detecting circuit 26 happens to be broken. The logic "NAND" gate circuit 94 has an output terminal connected to a logic negation circuit 96 so that the logic 0 or 1 signal appearing at the output terminal of the "NAND" gate circuit 94 is inverted into a logic 1 or 0 signal, respectively. The logic 1 and 0 output signals thus delivered from the negation circuit 96 correspond to the previously mentioned first and second output signals $S_1$ and $S_2$, respectively, of the wire breakage detecting circuit 28. The wire breakage detecting circuit 28 produces its logic 1 output signal $S_1$ in the absence of breakage in any of the lines or wires 14a to 14d and produces its logic 0 output signal $S_2$ in the presence of breakage in at least one of the lines or wires 14a 14d. Breakage of the line or wire 14e connecting the third output terminal 60 of the alcohol level detecting circuit 26 to ground is monitored as an increase in the potential appearing at each of the first input terminals 66a and 68a of the first and second comparator circuits 66 and 68 of the discriminating circuit 30 as will be discussed later.

The output signal $S_1$ or $S_2$ from the wire breakage detecting circuit 28 and the output signal $R_1$ or $R_2$ from the discriminating circuit 30 are fed to the logic control circuit 32 which comprises a logic "NAND" gate circuit 98 having a first input terminal 98a connected to the output terminal of the negation circuit 84 of the discriminating circuit 30 and a second input terminal 98b connected to the negation circuit 96 of the wire breakage detecting circuit 28. The "NAND" gate circuit 98 thus produces a logic 0 output signal when supplied with the logic 1 signals $R_1$ and $S_1$ from the discriminating circuit 30 and the wire breakage detecting circuit 28, respectively, and to produce a logic 1 signal when supplied with the logic 0 signal $R_2$ from the discriminating circuit 30 and/or the logic 0 signal $S_2$ from the wire breakage detecting circuit 28. The logic "NAND" circuit 98 has an output terminal connected to a logic negation circuit 100 so that the logic 0 or 1 signal appearing at the output terminal of the "NAND" gate circuit 98 is inverted into a logic 1 or 0 signal, respectively, at the output terminal of the negation circuit 100. The logic 1 and 0 output signals thus delivered from the negation circuit 100 correspond to the previously mentioned first and second output signals $T_1$ and $T_2$, respectively, of the logic control circuit 32. The logic 1 or 0 output signal $T_1$ $T_2$ thus delivered from the control circuit 32 is fed to the driver circuit 34 which maintains the previously mentioned locking device inoperative when supplied with the logic 1 signal $T_1$ from the control circuit 32 and to actuate the locking device into an operative condition when supplied with the logic 0 signal from the control circuit 32. The detailed construction of the driver circuit 32 to achieve these functions will be obvious to those skilled in the art and it is rather immaterial for the understanding of the present invention so that no description thereof will be herein given.

The operation of the exhalation inspecting apparatus embodying the present invention will now be described with concurrent reference to FIGS. 1 to 3, especially FIGS. 1 and 3.

When an intending driver of a vehicle is seated on the driver's seat and locks the door of the vehicle, then the switches responsive to the locked condition of the door and the seated condition of the intending driver are actuated to close the normally open switch 38 of the power source circuit 24. A d.c. voltage is consequently supplied from the d.c. power source or battery 36 to the voltage regulator 40 through the switch 38 thus closed. The d.c. voltage is increased or decreased by the voltage regulator 40 and voltages thus modified are fed from the first and second output terminals 42 and 44 of the voltage regulator 40 to the first and second input terminal 46 and 48, respectively, of the alcohol level detecting circuit 26. The voltage appearing at the first input terminal 46 of the alcohol level detecting circuit 26 is impressed on the alcohol sensing unit 50 so that a current flow through the heating element 50b of the unit 50 and produces heat in the element 50b. The alcohol-sensitive element 50a of the sensing unit 50 is heated by the heat emanated from the heating element 50b located in the vicinity of the alcohol-sensitive element 50a and becomes ready to sense an alcoholic atmosphere. The voltage fed to the second input terminal 48 of the alcohol level detecting circuit 26 is applied to the first and accordingly second thermistors 54 and 56 of the detecting circuit 26.

If, under these conditions, the intending driver, who is in this instance assumed to be either sober or only temporately intoxicated, blows into the blow-in tube 10, the alcohol-sensitive element 50a of the sensing unit 50 located within the blow-in tube 50 is saturated with the air exhaled by the subject and is caused to have its resistance diminished if the exhaled air contains alcohol, producing at the first output terminal 52 of the alcohol level detecting circuit 26 a voltage $V_1$ which is indicative of an alcohol concentration detected by the alcohol-sensitive element 50a. The voltage $V_1$ is supplied to the first comparator circuit 66 of the discriminating circuit 30 through the first input terminal 66a of the comparator circuit 66 and is compared with the reference voltage $E_1$ which is impressed on the second input terminal 66b of the comparator circuit 66. Because, in this instance, the subject blowing into the blow-in tube 10 is assumed to be sober or only moderately intoxicated, the alcohol concentration detected by the alcohol-sensitive element 50a is lower than the previously mentioned allowable limit so that the voltage $V_1$ fed to the first comparator circuit 66 is lower than the reference voltage $E_1$ indicative of the allowable limit of the alcohol concentation. The first comparator circuit 66 therefore produces its logic 0 output signal and, accordingly, the negation circuit 76 connected to the comparator circuit 66 produces its logic 1 output signal. The exhaled air blow into the blow-in tube 10 is also applied to the first thermistor 54 of the alcohol level detecting circuit 26 and cools down the thermistor 54, giving rise to an increase in the resistance of the thermistor 54.

Across the first thermistor 54 is consequently produced a voltage $V_2$ which is diminished in proportion to the volume of the exhaled air blown into the blow-in tube 10. The voltage $V_2$ is applied to the second comparator circuit 68 of the discriminating circuit 30 through the second output terminal 58 of the alcohol level detecting circuit 26 and the first input terminal 68a of the comparator circuit 68. The voltage $V_2$ thus fed to the comparator circuit 68 is compared with the reference voltage $E_2$ which is impressed on the second input terminal 68b of the comparator circuit 68. If, in this instance, the volume of the exhaled air blown into the blow-in tube 10 is larger than the predetermined minimum limit which make the result of the inspection reliable, the voltage $V_2$ is lower than the reference volage $E_2$ so that the comparator circuit 68 produces its logic 1 output signal. Under these conditions, the "NAND" gate circuit 82 of the discriminating circuit 30 is supplied with the logic 1 signals at both of its first and second input terminals 82a and 82b and produces its logic 0 output signal, thereby delivering the logic 0 signal $R_1$ at the output terminal of the discriminating circuit 30.

When, on the other hand, the voltage $V_1$ is delivered from the first output terminal 52 of the alcohol level detecting circuit 26, the first transistor 86 of the wire breakage detecting circuit 28 is rendered conductive and passes the voltage from the first output terminal 42 of the voltage regulator 40 to the first input terminal 94a of the logic "NAND" gate circuit 94 of the wire breakage detecting circuit 28 through the collector-emitter circuit of the transistor 86. Likewise, the second transistor 88 of the wire breakage detecting circuit 28 is rendered conductive by the voltage $V_2$ delivered from the second output terminal 58 of the alcohol level detecting circuit 26 so that the voltage appearing at the second output terminal 44 of the voltage regulator 40 is passed through the collector-emitter circuit of the transistor 88 to the second input terminal 94b of the "NAND" gate circuit 94 of the wire breakage detecting circuit 28. The logic "NAND" gate circuit 94 is, in this manner, supplied with input voltages at both of its first and second input terminals 94a and 94b and produces its logic 0 output signal delivering the logic 1 signal $S_1$ at the output terminal of the wire breakage detecting circuit 28.

When the wire breakage detecting circuit 28 and the discriminating circuit 30 thus produce their respective logic 1 output signals $S_1$ and $R_1$, the logic "NAND" gate circuit 98 of the control circuit 32 produces its logic 0 output signal so that the control circuit 32 produces its logic 1 output signal $T_1$. The logic 1 signal $T_1$ thus delivered from the control circuit 32 is fed to the driver circuit 34 which is accordingly actuated to make the previously mentioned locking device of the vehicle inoperative. The subject or the intending driver of the vehicle is now permitted to start the vehicle in usual manners.

In case, however, the subject or intending driver blowing into the blow-in tube 10 shown in FIG. 1 has been drinking heavily and accordingly the concentration of alcohol in the exhaled air blown into the alcohol-sensitive element 50a exceeds the previously mentioned allowable limit, then the voltage $V_1$ delivered from the first output terminal 52 of the alcohol level detecting circuit 26 to the first comparator circuit 66 of the discriminating circuit 30 is higher than the reference voltage $E_1$ indicative of such an allowable limit. Under these conditions, the final comparator circuit 66 of the discriminating circuit 30 produces its logic 1 output signal, which is converted into a logic 0 signal by the negation circuit 76. The logic "NAND" gate circuit 82 of the discriminating circuit 30 is thus supplied with the logic 0 signal at its first input terminal 82a and is consequently caused to produce its logic 1 output signal irrespective of the signal delivered to its second input terminal 82b from the second comparator circuit 68. The logic 1 output signal of the "NAND" gate circuit 82 is inverted by the negation circuit 84 of the discriminating circuit 30, which therefore produces its logic 0 output signal $R_2$. The logic "NAND" gate circuit 98 of the control circuit 32 is thus supplied with the logic 0 at its first input terminal 98a and produces its logic 1 output signal irrespective of the signal applied to its second input terminal 98b from the wire breakage detecting circuit 28. The control circuit 32 now produces its logic 0 output signal $T_2$ so that the driver circuit 34 is actuated to render the locking device of the vehicle operative. The intending driver is in this manner prohibited from driving the vehicle which is held inoperative by the locking device.

In case the volume of the exhaled air blown into the blow-in tube 10 is deficient and is short of the predetermined minimum limit as previously mentioned, the voltage $V_2$ delivered from the second output terminal 58 of the alcohol level detecting circuit 26 to the first input terminal 68a of the second comparator circuit 68 of the discriminating circuit 30 is higher than the reference voltage $E_2$ which is impressed on the second input terminal 68b of the comparator circuit 68, which accordingly produces its logic 0 output signal. The logic "NAND" gate circuit 82 of the discriminating circuit 30 is thus supplied with a logic 0 signal at its second input terminal 82b and is caused to produce its logic 1 output signal irrespective of the signal applied to the first input terminal 82a thereof from the second comparator circuit 68. The logic "NAND" gate circuit 98 of the control circuit 32 thus receives the logic 0 signal $R_2$ at its first input terminal 98a and produces its logic 1 output signal irrespective of the signal which is applied to the second input terminal 98b thereof from the wire breakage detecting circuit 28. The control circuit 32 thus produces its logic 0 output signal $T_2$ so that the driver circuit 34 is actuated to render the locking device of the vehicle operative.

The vehicle is in these manners prevented from being started against the intending driver's will if he has been drinking heavily or if he blows, either unconsciously or on purpose, into the blow-in tube a volume smaller than the predetermined minimum limit. In case the intending driver or subject has blown into the blow-in tube a deficient volume of exhaled air without purpose, he may try on another inspection by blowing into the blow-in tube a sufficient volume of exhaled air so as to render the locking device of the vehicle inoperative.

The discussion thus far made in respect of the operation of the exhalation inspecting apparatus embodying the present invention has been based on the assumption that the lines 14a to 14e connected to the alcohol level detecting circuit 26, viz., the lines or wires 14 leading from the blow-in tube 10 shown in FIG. 1 are all free from breakage. In the event at least one of the lines 14a and 14c connected to the first input and output terminals 46 and 52, respectively of the alcohol level detecting circuit 26, happens to be broken, the sensing unit 50 of the alcohol level detecting circuit 26 is rendered de-energized although the normally open switch 38 is in closed condition. The potential at the first input terminal 66a of the first comparator circuit 66 is thus reduced below the reference signal $E_1$ applied to the second input terminal 66b of the comparator circuit 66, which consequently produces its logic 0 output signal as in the case where the alcohol concentration of the exhaled air inspected is lower than the allowable limit. With the line 14a and/or the line 14c broken, however, the base electrode of the first transistor 86 of the wire breakage detecting circuit 28 is disconnected from the first output terminal of the voltage regulator 40 and the transistor 86 is rendered nonconductive. The "NAND" gate circuit 94 of the wire breakage detecting circuit 28 is therefore caused to produce its logic 1 output signal in the absence of the voltage at the first input terminal 94a thereof irrespective of the signal appearing at the second input terminal 94b. The wire breakage detecting circuit 28 thus produced its logic 0 output signal $S_2$ so that the "NAND" gate circuit 98 of the control circuit 32 produces its logic 1 output signal in the presence of the logic 0 signal at its second input terminal 98b and regardless of the signal which is impressed on the first input terminal 98a from the discriminating circuit 30. The control circuit 32 thus produces its logic 0 output signal $T_2$, actuating the driver circuit 34 to render the locking device of the vehicle operative. In case, on the other hand, breakage takes place in the line 14b and/or 14d which are connected to the second input and output terminals 48 and 58 of the alcohol level detecting circuit 26, then the first and second thermistors 54 and 56 of the detecting circuit 26 are rendered de-energized. The potential at the first input terminal 68a of the second comparator circuit 68 is thus reduced below the reference voltage $E_2$ impressed upon the second input terminal 68b of the comparator circuit 68 as if the first thermistor 54 were blown with a sufficient volume of exhaled air. Under these conditions, however, the base electrode of the second transistor 88 of the wire breakage detecting circuit 28 is disconnected from the second output terminal 44 of the voltage regulator 40 and is thus de-energized so that the transistor 88 is rendered non-conductive. The "NAND" gate circuit 94 of the wire breakage detecting circuit 28 is therefore caused to produce its logic 1 output signal and, accordingly, the wire breakage detecting circuit 28 produces its logic 0 output signal $S_2$ in the presence of the zero potential at the second input terminal 94b of the "NAND" gate circuit 94 and irrespective of the voltage appearing at the first input terminal 94a of the "NAND" gate circuit 94. The control circuit 32 is, thus, caused to produce its logic 0 output signal $T_2$ irrespective of the signal delivered from the discriminating circuit 30, as in the case where the line 14a and/or the line 14c is broken.

In the event the line 14e leading from the third output terminal 60 of the alcohol level detecting circuit 26 happens to be broken, increased voltages are developed across the alcohol-sensitive element 50a of the sensing unit 50 and the first thermistor 54, respectively, of the detecting circuit 26. The increased voltages are impressed on the first input terminals 66a and 68a of the first and second comparator circuits 66 and 68, respectively, of the discriminating circuit 30 and exceed the reference voltages $E_1$ and $E_2$ impressed on the second input terminals 66b and 68b of the comparator circuits 66 and 68, respectively. The first comparator circuit 66 thus produces its logic 1 output signal as if an alcohol concentration higher than the allowable limit were detected by the sensing unit 50, whereas the second comparator circuit 68 produces its logic 0 output signal as if a deficient volume of exhaled air were blown into the blow-in tube 10. The logic 1 output signal from the first comparator circuit 66 is inverted by the negation circuit 76 so that the "NAND" gate circuit 82 is supplied with logic 0 signals at both of its input terminals 82a and 82b and produces its logic 1 output signal. The logic 1 signal thus appearing at the output terminal of the "NAND" gate circuit 82 is inverted by the negation circuit 84 and, as a consequence, the discriminating circuit 30 produces its logic 0 output signal $R_2$. The control circuit 32 thus produces its logic 0 output signal $T_2$ irrespective of the signal delivered from the wire breakage detecting circuit 28 and actuates the driver circuit 34, making the locking device of the vehicle operative. The vehicle is in these manners held inoperative not only if the intending driver has been heavily drinking or has failed to properly blow into the blow-in tube but also when any one of the lines connected to the input and output terminals of the alcohol level detecting circuit 26 and leading from the blow-in tube 10 is broken.

The diodes 62 and 64 are provided in the alcohol level detecting circuit 26 for the purpose of preventing a current from flowing from the second input terminal 48 to the base electrode of the first transistor 86 via the line interconnecting the second thermistor 56 and the heating element 50b of the alcohol sensing unit 50 in the event the line 14a alone happens to be broken and preventing a current from flowing from the first input terminal 46 to the base electrode of the second transistor 88 via the above-mentioned line interconnecting the heating element 50b of the alcohol sensing unit 50 and the second thermistor 56.

While only one preferred embodiment of the exhalation inspecting apparatus according to the present invention has been described in detail, it should be borne in mind that such an embodiment is merely by way of example and may therefore be subject to change and modification where desired. It should also be remembered that, although the exhalation inspecting apparatus embodying the present invention has been assumed to be used in combination with a locking device which forcibly holds the vehicle inoperative when actuated, the exhalation inspection apparatus according to the present invention may be utilized solely for the purpose of inspecting an alcohol concentration in the exhaled air of a subject who may not necessarily be an intending driver of a vehicle.

What is claimed is:

1. An exhalation inspecting apparatus comprising power supply means, an alcohol level detecting circuit connected to the power supply means by a first set of wires and operative to produce a first output voltage indicative of an alcohol concentration of air exhaled by a subject and a second output voltage indicative of the volume of the subject's exhaled air, a discriminating circuit connected to said alcohol level detecting circuit by a second set of wires and operative to produce a first output signal if said first output voltage is indicative of an alcohol concentration lower than a predetermined allowable limit and said second output voltage is indicative of a volume of exhaled air larger than a predetermined minimum limit and a second output signal if said first output voltage is indicative of an alcohol concentration higher than said allowable limit and/or said second output voltage is indicative of a volume of exhaled air smaller than said minimum limit, a wire breakage detecting circuit responsive to breakage of any one of said wires and operative to produce a first output signal in the absence of breakage in said wires and a second output signal in response to breakage of at least one of said wires, and a control circuit responsive to the signals from said discriminating circuit and said wire breakage detecting circuit for producing a first output signal in the presence of both of the first output signals from the discriminating circuit and the wire breakage detecting circuit and a second output signal in the presence of at least one of the second output signals from the discriminating circuit and the wire breakage detecting circuit.

2. An exhalation inspecting apparatus as set forth in claim 1, in which said power supply means has first and second output terminals and said alcohol level detecting circuit has first and second input terminals connected to said first and second output terminals of said power supply means through said first set of wires respectively and first and second output terminals connected to said discriminating circuit through said second set of wires, said alcohol level detecting circuit comprising first detecting means connected between the first input and output terminals of the alcohol level detecting circuit and responsive to alcoholic atmosphere contained in the subject's exhaled air for delivering said first output voltage from said first output terminal of the alcohol level detecting circuit and second detecting means connected between the second input and output terminals of the alcohol level detecting circuit and responsive to the volume of the subject's exhaled air for thereby delivering said second output voltage from said second output terminal of the alcohol level detecting circuit.

3. An exhalation inspection apparatus as set forth in claim 1, in which said alcohol level detecting circuit comprises first detecting means operative to produce said output voltage which has a tendency of increasing as the detected alcohol concentration increases and second detecting means operative to produce said second output voltage which has a tendency of diminishing as the detected volume of the exhaled air increases, said discriminating circuit comprising first comparing means for being supplied with said first output voltage and with a first reference voltage indicative of said predetermined allowable limit of the alcohol concentration and producing a first output signal if said first output voltage is lower than said first reference voltage and a second output signal if the first output voltage is higher than said first reference voltage, second comparing means for being supplied with said second output voltage and with a second reference voltage indicative of said predetermined minimum limit of the volume of the exhaled air and producing a first output signal if said second output voltage is lower than said second reference voltage and a second output signal if the second output voltage is higher than said second reference voltage, and circuit means for producing said first output signal of the discriminating circuit in the presence of both of the first output signal from said first and second comparing means and said second output signal of the discriminating circuit in the presence of at least one of the second output signals from the first and second comparing means.

4. An exhalation inspecting apparatus as set forth in claim 1, in which said power supply means has first and scond output terminals and said alcohol level detecting circuit has first and second input terminals connected to the first and second output terminals through said first set of wires, respectively, and first and second output terminals connected to said discriminating circuit through said second set of wires, said wire breakage detecting circuit comprising first switching means connected to said first output termnal of said power supply means and having a control electrode connected to said first input terminal through said first output terminal of the alcohol level detecting circuit for rendering the first switching means conductive in the absence of breakage in each of the wires connected to the first input and output terminals of the alcohol level detecting circuit and non-conductive in the presence of breakage in at least one of the wires connected to said first input and output terminals of the alcohol level detecting circuit, second switching means connected to said second output terminal of said power supply means and having a control electrode connected to said second input terminal through said second output terminal of the alcohol level detecting circuit for rendering the second switching means conductive in the absence of breakage in each of the wires connected to said second input and output terminals of the alcohol level detecting circuit and non-conductive in the presence of breakage in at least one of the wires connected to the second input and output terminals of the alcohol level detecting circuit, and circuit means having first and second input terminals respectively connected over said first and second switching means to said first and second output terminals of said power supply means for producing said first output signal of the wire breakage detecting circuit when both of said first and second switching circuits are conductive and said second output signal of the wire breakage detecting circuit when at least one of said first and second switching means is non-conductive.

5. An exhalation inspecting circuit as set forth in claim 2, in which said first detecting means comprises an alcohol-sensitive element connected between said first input and output terminals of the alcohol level detecting circuit and operative to have its resistance reduced when subjected to alcoholic atmosphere under heated condition and a heating element connected at one end to said first input terminal of the alcohol level detecting circuit and at the other end to ground and positioned in the vicinity of said alcohol-sensitive element for heating the alcohol-sensitive element when energized from said power supply means through said first input terminal of the alcohol level detecting circuit, and in which said second detecting means comprises a temperature-sensitive resistance-variable element connected at one end to said first input terminal and at the other to said second output terminal of the alcohol level detecting circuit and operative to have its resistance increased when blown with the subject's exhaled air.

6. An exhalation inspecting apparatus as set forth in claim 5, in which said temperature-sensitive resistance-variable element is grounded at said other end.

7. An exhalation inspecting apparatus as set forth in claim 6, in which said temperature-sensitive resistance-variable element is grounded through a second temperature-sensitive resistance-variable element.

8. An exhalation inspecting apparatus as set forth in claim 7, in which said heating element of said first detecting means and said second temperature-sensitive resistance-variable element are connected in parallel to ground through first and second diodes, respectively, which are connected together in mutually forward directions.

9. An exhalation inspecting apparatus as set forth in claim 8, in which said diodes have respective cathode terminals connected to ground through a single wire.

10. An exhalation inspecting apparatus as set forth in claim 7, in which each of said temperature-sensitive resistance-variable elements is a thermistor.

11. An exhalation inspecting apparatus as set forth in claim 9, further comprising an exhalation blow-in tube into which the subject is to blow with exhaled air, said first and second detecting means being positioned within said blow-in tube so that all of said wires lead from the blow-in tube.

12. An exhalation inspecting apparatus as set forth in claim 3, in which said first comparing means comprises a comparator circuit having a first input terminal connected to said first output terminal of said alcohol level detecting circuit and a second input terminal connected to a source of said first reference voltage and operative to produce a logic 0 output signal when the first output voltage is lower than said first reference voltage and a logic 1 output signal when the first output voltage is higher than said first reference voltage and a logic negation circuit connected to the output terminal of said comparator circuit for producing a logic 1 output signal as said first output signal of said first comparing means responsive to the logic 0 output signal from said comparator and a logic 0 output signal as said second output signal of the first comparing means responsive to the logic 1 output signal from said comparator circuit, and in which said second comparing means comprises a comparator circuit having a first input terminal connected to said second output terminal of said alcohol level detecting circuit and a second input terminal connected to a source of said second reference voltage and operative to produce a logic 1 output signal as said first output signal of said second comparing means when the second output voltage is lower than said second reference voltage and a logic 0 output signal as said second output signal of the second comparing means when said second output voltage is higher than said second reference voltage.

13. An exhalation inspecting apparatus as set forth in claim 12, in which said circuit means of said discriminating circuit comprises a logic "NAND" gate circuit having a first input terminal connected to said logic negation circuit and a second input terminal connected to the comparator circuit of said second comparing means and operative to produce a logic 0 output signal in the presence of logic 0 signals at the first and second input terminals thereof and to produce a logic 1 output signal in the presence of a logic 0 signal at at least one of the first and second input terminals thereof, and a logic negation circuit connected to the output terminal of said logic "NAND" gate circuit for producing a logic 1 output signal as said first output signal of the discriminating circuit responsive to the logic 0 output signal from said "NAND" gate circuit and a logic 0 output signal as said second output signal of the discriminating circuit responsive to the logic 1 output signal from said "NAND" gate circuit.

14. An exhalation inspecting apparatus as set forth in claim 4, in which said first switching means comprises a transistor having a collector-emitter circuit connected between said first output terminal of said power supply means and said first input terminal of said circuit means and a base electrode constituting said control electrode connected to said first output terminal of said alcohol level detecting circuit and in which said second switching means comprises a transistor having a collector-emitter circuit connected between said second output terminal of said power supply means and said second input terminal of said circuit means and a base electrode constituting said control electrode connected to said second output terminal of said alcohol level detecting circuit.

15. An exhalation inspecting apparatus as set forth in claim 14, in which said circuit means of said wire breakage detecting circuit comprises a logic "NAND" gate circuit having input terminals respectively constituting said first and second input terminals of the circuit means for producing a logic 0 output signal when both of said transistors are conductive and a logic 1 output signal when at least one of said transistors is non-conductive, and a logic negation circuit connected to the output terminal of said "NAND" gate circuit for producing a logic 1 output signal as said first output signal of the wire breakage detecting circuit responsive to the logic 0 output signal from said "NAND" gate circuit and a logic 0 output signal as said second output signal of the wire breakage detecting circuit responsive to the logic 1 output signal from said "NAND" gate circuit.

16. An exhalation inspecting apparatus as set forth in Claim 1, in which said discriminating circuit is operative to produce logic 1 and 0 output signals as said first and second output signals, respectively, of said discriminating circuit and said wire breakage detecting circuit is operative to produce logic 1 and 0 output signals as said first and second output signals, respectively, of the wire breakage detecting circuit, said control circuit comprising a logic "NAND" gate circuit having a first input terminal connected to the output terminal of said discriminating circuit and a second input terminal connected to the output terminal of said wire breakage detecting circuit for producing a logic 0 output signal in the presence of logic 1 signals at both of the first and second input terminals thereof and a logic 1 output signal in the presence of a logic 0 signal at at least one of the first and second input terminals thereof, and a logic negation circuit connected to the output terminal of said "NAND" gate circuit for producing a logic 1 output signal as said first output signal of said control circuit responsive to the logic 0 output signal from said "NAND" gate circuit and a logic 0 output signal as said second output signal of the control circuit responsive to the logic 1 output signal from said "NAND" gate circuit.

17. A locking device for holding a vehicle inoperative comprising an exhalation inspecting apparatus which comprises an exhalation blow-in tube into which an intending driver of the vehicle is to blow with exhaled air for inspection of alcohol content in the exhaled air, a flexible cord leading from the blow-in tube and containing therein a plurality of wires including first and second sets of wires, power supply means, an alcohol level detecting circuit located within said blow-in tube and electrically connected to said power supply means by said first set of wires, said detecting circuit being operative to produce a first output voltage indicative of an alcohol concentration of the exhaled air blown into said blow-in tube and a second output voltage indicative of the volume of the exhaled air blown into said blow-in tube, a discriminating circuit connected to said alcohol level detecting circuit by said second set of wires and operative to produce a first output signal if said first output voltage is indicative of an alcohol concentration lower than a predetermined allowable limit and said second output voltage is indicative of a volume of exhaled air larger than a predetermined minimum limit and a second output signal is said first output voltage is indicative of an alcohol concentration higher than said predetermined allowable limit and/or said second output voltage is indicative of a volume of exhaled air smaller than said predetermined minimum limit, a wire breakage detecting circuit responsive to breakage of any of said wires in said flexible cord and operative to produce a first output signal in the absence of breakage in said wires and a second output signal in response to breakage of at least one of the wires in said cord, a control circuit responsive to the signals from the discriminating circuit and the wire breakage detecting circuit for producing a first output signal in the presence of both of the first output signals from the discriminating circuit and the wire breakage circuit and a second output signal in the presence of at least one of the second output signals from said discriminating circuit and said wire breakage detecting circuit, and vehicle locking means for rendering the vehicle operative responsive to the first output signal from said control circuit and inoperative responsive to the second output signal from said control circuit.

18. A locking device as set forth in claim 17, in which said blow-in tube has a housed condition and an operative condition moved out of said housed condition and which further comprises biasing means for urging said cord to be taut and urging said blow-in tube toward said housed condition.

19. A locking device as set forth in claim 17, in which said power supply means comprises a normally open switch which is operative to close responsive to the locked condition of a door of the vehicle and the seated condition of the intending driver on the driver's seat of the vehicle.

* * * * *